US00PP35006P3

(12) United States Plant Patent
Bentley

(10) Patent No.: US PP35,006 P3
(45) Date of Patent: Feb. 28, 2023

(54) ***ANISODONTEA* PLANT NAMED 'IB609-5'**

(50) Latin Name: *Anisodontea capensis*
Varietal Denomination: IB609-5

(71) Applicant: Plant Growers Australia Pty. Ltd., Wonga Park (AU)

(72) Inventor: Howard Bentley, Wonga Park (AU)

(73) Assignee: Plant Growers Australia Pty. Ltd., Wonga Park (AU)

( * ) Notice: Subject to any disclaimer, the term of this patent is extended or adjusted under 35 U.S.C. 154(b) by 0 days.

(21) Appl. No.: 17/803,317

(22) Filed: May 9, 2022

(65) Prior Publication Data

US 2022/0361388 P1 Nov. 10, 2022

Related U.S. Application Data

(60) Provisional application No. 63/185,684, filed on May 7, 2021.

(51) Int. Cl.
*A01H 5/02* (2018.01)
*A01H 6/60* (2018.01)

(52) U.S. Cl.
USPC ..... Plt./263.1
CPC ..... *A01H 6/60* (2018.05)

(58) Field of Classification Search
USPC ..... Plt./263.1
CPC ..... A01H 6/60; A01H 5/02
See application file for complete search history.

*Primary Examiner* — Keith O. Robinson
(74) *Attorney, Agent, or Firm* — Samuel R. McCoy, Jr.

(57) ABSTRACT

A new and distinct *Anisodontea capensis* plant named 'IB609-5' which is characterized by a compact, densely foliaged growth habit, an abundance of dark red to red-purple flowers with dark red centers and dark red reticulate veins, and the stability of these characteristics from generation to generation.

2 Drawing Sheets

Latin name of the genus and species: The Latin name of the genus and species of the novel variety disclosed herein is *Anisodontea capensis*.

Variety denomination: The inventive variety of *Anisodontea capensis* disclosed herein has been given the variety denomination 'IB609-5'.

BACKGROUND OF THE INVENTION

Parentage: 'IB609-5' is a seedling selection resulting from the controlled cross pollination of *Anisodontea capensis* 'Dryspell Raspberry' (not patented), the seed parent, with *Anisodontea capensis* 'El Royo' (not patented), the pollen parent. In the late summer of 2016 the above pollination occurred at the breeding site located in Wonga Park, Victoria, Australia. Seeds were collected from 'Dryspell Raspberry', sown, and seedlings were grown out to maturity, during the spring of 2016. One of the resulting plants was observed to exhibit medium to dense foliage, and shorter plant height, as well as an abundance of dark red-purple flowers with a red to very dark red-purple centers. The seedling was isolated for further evaluation to confirm the distinctness and stability of the characteristics first observed. Upon confirmation of distinctness and stability, 'IB609-5' was selected for commercialization.

Asexual Reproduction: 'IB609-5' was first asexually reproduced by way of softwood stem cuttings in the spring of 2016 at the inventor's nursery in Wonga Park, Victoria, Australia. Through eight subsequent generations, the unique features of this cultivar have proven to be stable and true to type.

SUMMARY OF THE INVENTION

The following characteristics have been repeatedly observed and represent the distinguishing characteristics of the new *Anisodontea capensis* plant, 'IB609-5'. These traits, in combination, distinguish 'IB609-5' as a new and distinct cultivar.

1. 'IB609-5' exhibits a compact and densely-foliaged growth habit; and
2. 'IB609-5' exhibits an abundance of flowers; and
3. 'IB609-5' exhibits dark red to red-purple flower petals which are colored dark red near the base; and
4. 'IB609-5' exhibits flower petals which are veined very dark red.

BOTANICAL DESCRIPTION OF THE PLANT

Figure 1:
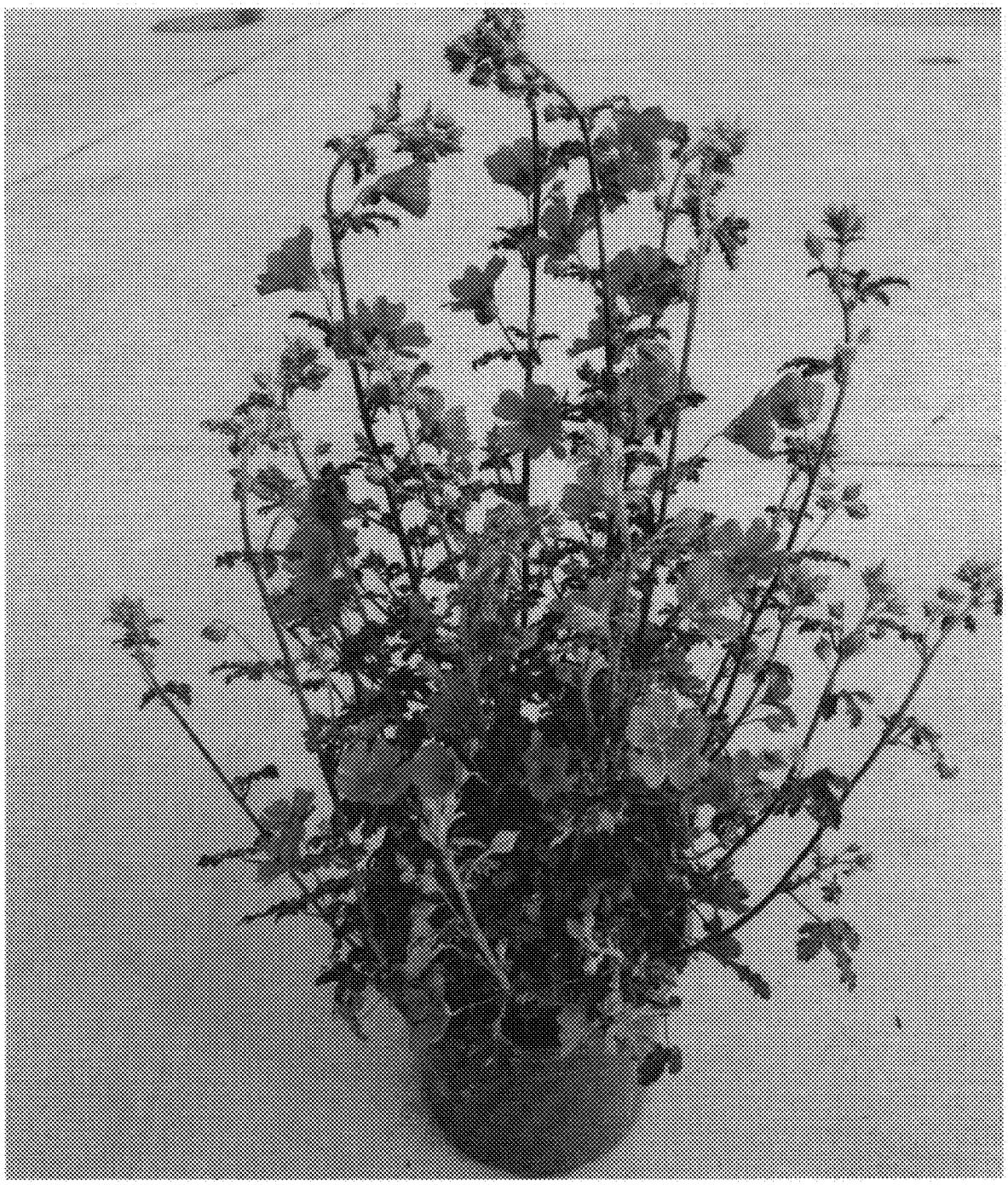
FIG. 1 illustrates, as nearly true as it is reasonably possible to make the same in color photographs of this type, an exemplary mature 'IB609-3' plant grown outdoors in Wonga Park, Victoria, Australia.
Figure 2:
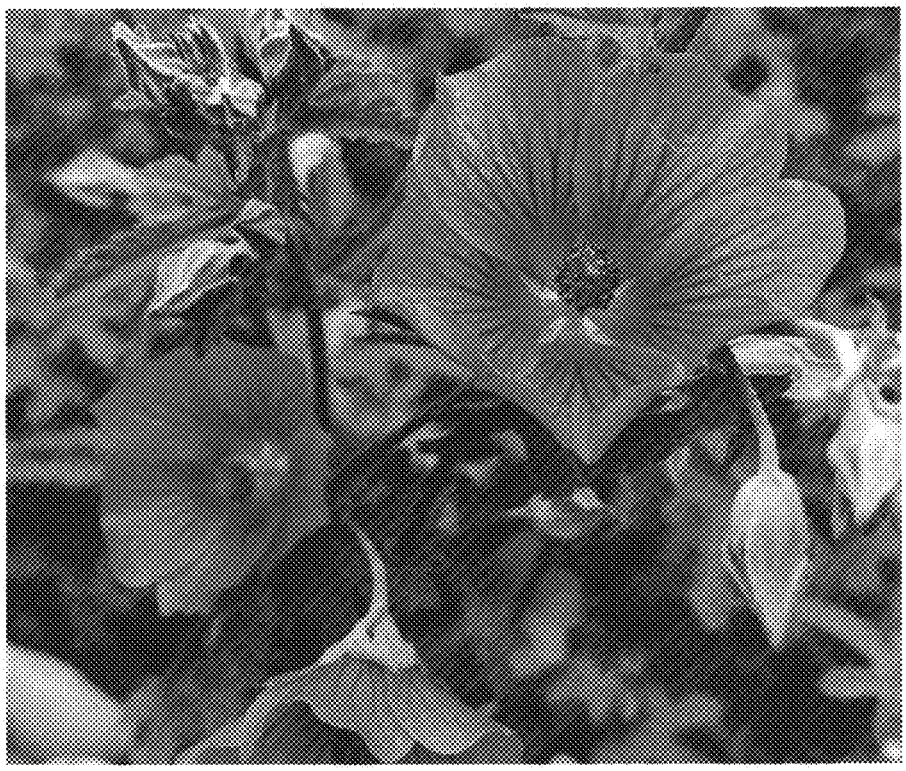
FIG. 2 illustrates, as nearly true as it is reasonably possible to make the same in color photographs of this type, exemplary flowers of a mature 'IB609-5' plant grown outdoors in Wonga Park, Victoria, Australia.

The following observations and measurements were made in August of 2022 and describe a 6-month-old 'IB609-5' plant grown outdoors in Greeleyville, S.C., in a 15 cm nursery container. The plant was allowed to grow with full sun exposure and maintained with regular overhead irrigation and slow-release granular fertilizer applications. Preventative disease and pest control measures were utilized in production.

Those skilled in the art will appreciate that certain characteristics will vary with older or, conversely, with younger plants. 'IB609-5' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 1986 (third edition).

A botanical description of 'IB609-5' and comparisons with the parents and most similar variety of common knowledge are provided below.

General plant description:

*Growth habit*.—Evergreen sub-shrub.

*Plant profile*.—Upright globular.

*Height*.—73.0 cm from the soil level to the top of the foliar plane.

*Plant spread*.—51.0 cm.

*Plant vigor*.—Moderately vigorous.

*Propagation type*.—Softwood stem cuttings.

*Time to produce a rooted cutting*.—Approximately 50 to 60 days to produce a rooted cutting at approximately 30 degrees Celsius.

*Time to produce a finished plant*.—24 weeks to produce a well-rooted 15 cm container.

*Disease resistance*.—Neither resistance nor susceptibility to typical *Anisodontea* pests and diseases has been observed.

*Environmental tolerances*.—Adapt to, at least, USDA Zones 9 through 11; moderate tolerance to rain; moderate tolerance to wind; drought tolerant once established.

Root system:

*General*.—Densely and freely branched rooting; roots are moderately fibrous.

*Distribution in the soil profile*.—Shallow to moderately deep.

Stem:

*General branching habit*.—Multiple main stems, freely branching from the base, with an abundance of lateral branches.

*Quantity of main stems per plant*.—6.

*Diameter of the main stem*.—1.2 cm at the base.

*Abundance of lateral branches*.—Abundant.

*Length of lateral branches*.—Approximately 45.0 cm.

*Diameter of lateral branches*.—Approximately 8 mm.

*Internode length*.—Ranging from 3.9 to 6.0 cm.

*Attitude of lateral branches*.—Upright and slightly outward.

*Aspect*.—Rounded.

*Texture, juvenile*.—Densely pubescent.

*Texture, mature*.—Moderately pubescent.

*Texture, oldest wood*.—Glabrous.

*Luster*.—Slightly glossy to matte.

*Strength*.—Strong.

*Color, juvenile lateral branches*.—Yellow-green, nearest to RHS 144B and suffused with 153B; becoming progressively suffused with greyed-purple with age, RHS 183C.

*Color, mature lateral branches*.—Greyed-purple, nearest to RHS 183C.

*Color, oldest wood*.—Nearest to a mixture of greyed-orange and grey-brown, RHS 165B and 199A.

Foliage:

*Arrangement*.—Alternate.

*Attachment*.—Petiolate.

*Division*.—Simple.

*Shape*.—Palmate.

*Aspect*.—Nearly flat.

*Attitude*.—Outward.

*Length*.—49.0 mm.

*Width*.—43.0 mm.

*Apex*.—Obtuse.

*Base*.—Truncate.

*Margins*.—Serrate; ciliate.

*Texture and pubescence, adaxial surface*.—Bullate and glabrous except for the veins which are pubescent.

*Texture and pubescence, abaxial surface*.—Bullate and glabrous except for the veins which are pubescent.

*Luster, adaxial surface*.—Slightly glossy.

*Luster, abaxial surface*.—Slightly glossy.

*Color*.—Juvenile foliage color, adaxial surface — Yellow-green, nearest to RHS 144A. Juvenile foliage color, abaxial surface — Yellow-green, nearest to RHS 144B. Mature leaf color, adaxial surface — Nearest to in between green and yellow-green, RHS 137A and 147A. Mature leaf color, abaxial surface — Yellow-green, nearest to RHS 147B.

*Venation*.—Type — Reticulate. Vein color, adaxial surface — Yellow-green, nearest to RHS 144A. Vein color, abaxial surface — Yellow-green, nearest to a mixture of RHS 146A and 146B.

*Petiole*.—Length — 16.0 mm. Diameter — 3.0 mm. Strength — Strong. Texture, adaxial and abaxial surfaces — Pubescent. Luster, adaxial and abaxial surfaces — Matte. Color — Yellow-green, nearest to in between RHS 144A and 146D, and becoming progressively suffused with greyed-purple with age, RHS 183C.

*Stipules*.—General — Two stipules are present at the base of each leaf. Shape — Narrowly deltoid. Length — 8.0 mm. Width — 4.0 mm at the widest point. Aspect — Concave. Apex — Acute. Base — Truncate. Margin — Entire; no undulation. Texture, adaxial — Pubescent. Texture, abaxial — Pubescent. Luster — Matte on both the adaxial and abaxial surfaces. Color, adaxial surface — Yellow-green, nearest to RHS 146D, and margined greyed-purple, RHS 184A. Color, abaxial surface — Yellow-green, RHS 146D, and margined greyed-purple, RHS 184A.

Inflorescence: No inflorescences; flowers borne singularly or in pairs at leaf axils.

Flower buds:

*Shape*.—Obovoid, with a pointed apex; pentangulate.

*Length*.—27.0 mm.

*Diameter*.—19.0 mm.

*Texture*.—Pubescent.

*Luster*.—Slightly glossy.

*Color*.—Yellow-green, nearest to in between RHS 144A and 146D, and suffused with greyed-purple, RHS 183A, along the margins and apices of the closed sepals.

Flowers:

*Shape, type*.—Rotate, with a single whorl of petals; petals overlapping.

*Attachment*.—Pedicellate.

*Flowering habit*.—Freely flowering from late spring through Autumn in USDA Hardiness Zone 9.

*Attitude*.—Outward.

*Flower longevity on plant*.—Approximately 5 days.

*Persistent or self-cleaning*.—Self-cleaning.

*Fragrance*.—Non-fragrant.

*Diameter*.—Diameter of the corolla is 68.0 mm.

*Depth*.—Depth of the corolla is 34.0 mm.

*Pedicels*.—Length — 21.0 mm. Width — 4.0 mm at the base. Strength — Moderately strong. Texture — Pubescent. Color — Yellow-green, nearest to a mixture of RHS 144C and 145A, and moderately suffused with greyed-red at anthesis, nearest to RHS 185B.

*Calyx*.—Shape — Rotate. Depth — 21.0 mm. Diameter — 24.5 mm. Sepals — Quantity — 5. Shape — Deltoid. Dimensions — 19.5 mm long and 10.0 mm wide at the widest point. Apex — Acute. Base — Fused. Margin — Entire. Texture — Pubescent. Luster — Matte. Color — Yellow-green, nearest to RHS 144A, and heavily suffused with greyed-red at anthesis, nearest to RHS 184B.

*Episepals*.—Quantity — 3. Shape — Narrowly deltoid. Dimensions — 10.0 mm long and 3.0 mm wide at the base. Apex — Acute. Base — Fused. Margin — Entire. Texture — Pubescent. Luster — Matte. Color — Yellow-green, nearest to a mixture of RHS 144A, and margined with greyed-red at anthesis, nearest to RHS 183B.

*Petals*.—Quantity — 5. Arrangement — Rotate. Length — 26.0 mm. Width — 28.0 mm. Shape — Near-obcordate. Aspect — Somewhat concaved to nearly flat. Apex — Retuse. Base — Attenuate. Margin — Entire; light undulation. Texture, inner surface — Glabrous; coriaceous. Texture, outer surface — Glabrous; coriaceous. Petal color — When opening, outer surface — Nearest to in between red and red-purple, RHS 54A and 58B; base of the petal is red, nearest to RHS 45A. When opening, inner surface — Nearest to in between red and red-purple, RHS 54A and 58B; base of the petal is red, nearest to RHS 45A. Fully opened, inner surface — Nearest to in between red and red-purple, RHS 54A and 58B; base of the petal is red, nearest to RHS 45A. Fully opened, outer surface — Nearest to in between red and red-purple, RHS 54A and 58B; base of the petal is red, nearest to RHS 45A. Petal venation color — Pattern — Reticulate. Inner surface — Red, nearest to RHS 53A. Outer surface — Red, nearest to RHS 53A.

Reproductive organs:

*Staminal column*.—Description — A staminal column bears an abundance of stamens along its distal portion and terminates with a lobed pistil; the style is enveloped within the staminal column. Length — 14.5 mm, excluding the lobed stigma. Width — 4.0 mm. Color — Nearest to in between red and red-purple, RHS 54A and 58B.

*Androecium*.—Stamens — Quantity — Approximately 80. Anthers — Attachment — Dorsifixed. Shape — Globular. Dimensions — 1.0 mm long and 0.75 to 1.0 mm wide. Color — Nearest to in between black and dark purple, RHS 202A and 79A, yet nearer to black. Filaments — Length —7.5 mm. Diameter — 0.75 mm. Color — Red-purple, RHS 65B. Amount of Pollen — Moderately abundant. Pollen color — Greyed-yellow, nearest to RHS 162C.

*Gynoecium*.—Pistil — Quantity — One. Length —15.0 mm. Style — Not visible within the staminal column. Stigma — Shape — Lobed, with approximately 12 lobes. Length — 8.5 mm. Width — 11.0 mm across the stigma lobes. Color — Red-purple, RHS 67B. Ovary position — Superior.

Seed and fruit: Seeds not observed.

Comparisons With the Parent Plants

Plants of the new cultivar 'IB609-5' differ from the seed parent and most similar variety known to the inventor, *Anisodontea capensis* 'Dryspell Raspberry' (not patented), in the following characteristics described in Table 1 below.

TABLE 1

| Characteristic | 'IB609-5' | 'Dryspell Raspberry' |
|---|---|---|
| Growth habit. | More compact and densely foliaged. | Less compact and less densely foliage. |
| General coloration of the flower petals. | Dark red to red-purple with dark red near the base. | Dark red-purple. |

Plants of the new cultivar 'IB609-5' differ from the pollen parent, *Anisodontea capensis* 'El Royo' (not patented), in the following characteristics described in Table 2 below.

TABLE 2

| Characteristic | 'IB609-5' | 'El Royo' |
|---|---|---|
| Plant height. | Shorter than the pollen 'El Royo'. | Taller than 'IB609-5'. |
| Foliage size. | Smaller than 'El Royo'. | Larger than 'IB609-5'. |
| Flower size. | Smaller than 'El Royo'. | Larger than 'IB609-5'. |
| General coloration of the flowers. | Dark red to red-purple with dark red near the base. | Red-purple. |

Plants of the new cultivar 'IB609-5' differ from the most similar variety of common knowledge, *Anisodontea capensis* 'New Princess' (not patented), in the following characteristics described in Table 3 below.

TABLE 3

| Characteristic | 'IB609-5' | 'New Princess' |
|---|---|---|
| Plant height. | Shorter than 'New Princess. | Taller than 'IB609-5'. |
| Flower size. | Larger than 'New Princess'. | Smaller than 'IB609-5'. |
| General coloration of the flowers. | Dark red to red-purple with dark red near the base. | Light red-purple. |
| General coloration of the floral veins. | A dark shade of red. | A light shade of red-purple. |

That which is claimed is:

1. A new and distinct variety of *Anisodontea capensis* plant named 'IB609-5', substantially as described and illustrated herein.

* * * * *